United States

Currey 4,065,208

Dec. 27, 1977

[54] OPHTHALMOSCOPE

[76] Inventor: Thomas A. Currey, 87 Wallace Road, Memphis, Tenn. 38117

[21] Appl. No.: 518,612

[22] Filed: Oct. 29, 1974

[51] Int. Cl.$^2$ ............................................. A61B 3/12
[52] U.S. Cl. ...................................... 351/6; 350/96 B; 351/16
[58] Field of Search ...................... 351/6, 16; 350/96 B

[56] References Cited

U.S. PATENT DOCUMENTS

| | | | |
|---|---|---|---|
| 3,630,602 | 12/1971 | Herbert | 351/16 |
| 3,664,730 | 5/1972 | Cardona | 351/6 |
| 3,698,099 | 10/1972 | Matsura | 351/6 |
| 3,770,342 | 11/1973 | Dudragne | 351/16 X |
| 3,780,979 | 12/1973 | Guillebon | 351/16 |
| 3,820,879 | 6/1974 | Frisen | 351/6 X |

FOREIGN PATENT DOCUMENTS

| | | | |
|---|---|---|---|
| 494,779 | 3/1954 | Italy | 351/6 |

*Primary Examiner*—Paul A. Sacher
*Attorney, Agent, or Firm*—John R. Walker, III

[57] ABSTRACT

An ophthalmoscope for allowing an observer to clearly and easily view the retina of a patient's eye. The ophthalmoscope has a hollow body member with an objective portion attached to one end thereof for placement over the patient's eye and with an ocular portion attached to the other end thereof for allowing the observer to view the patient's eye. The objective portion includes a contact lens member fixedly attached to the body member for contacting engagement with the cornea of the patient's eye. A light source directs light into the body member and against a deflection member positioned in the body member adjacent the objective portion. The deflection member directs the light from the light source and the line of sight from the ocular portion into the retina of the patient's eye. A magnification member is preferably positioned in the body member between the objective portion and the ocular portion for causing the patient's eye to be magnified as the observer views the patient's eye through the ocular portion.

3 Claims, 3 Drawing Figures

U.S. Patent       Dec. 27, 1977       4,065,208
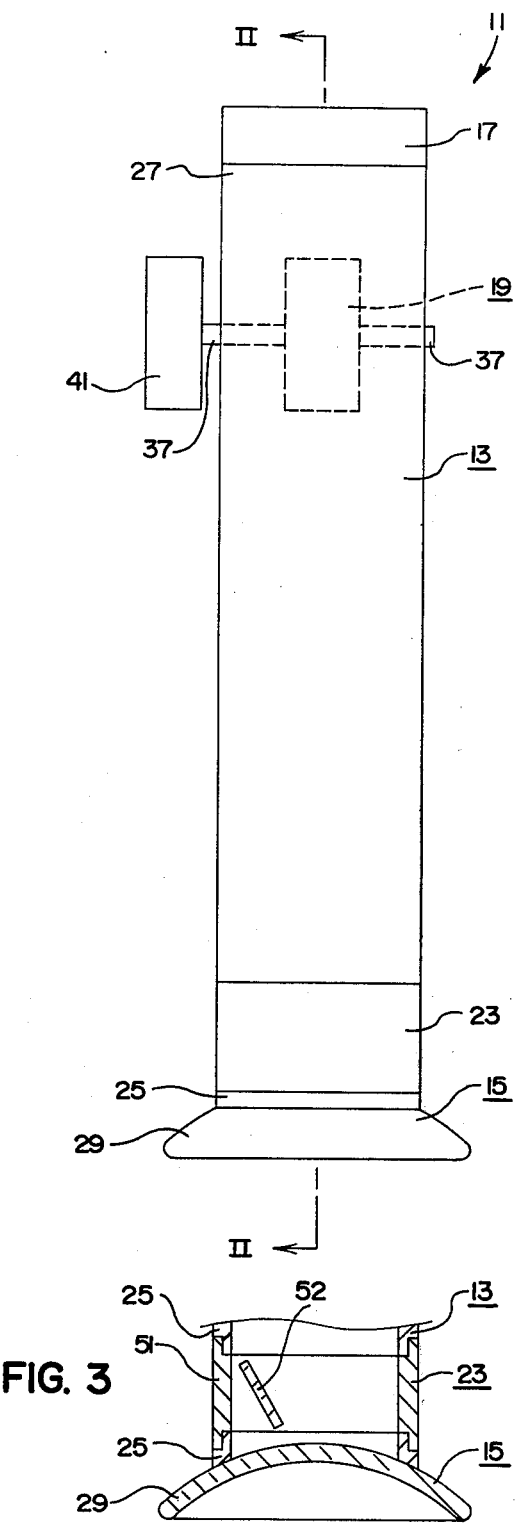
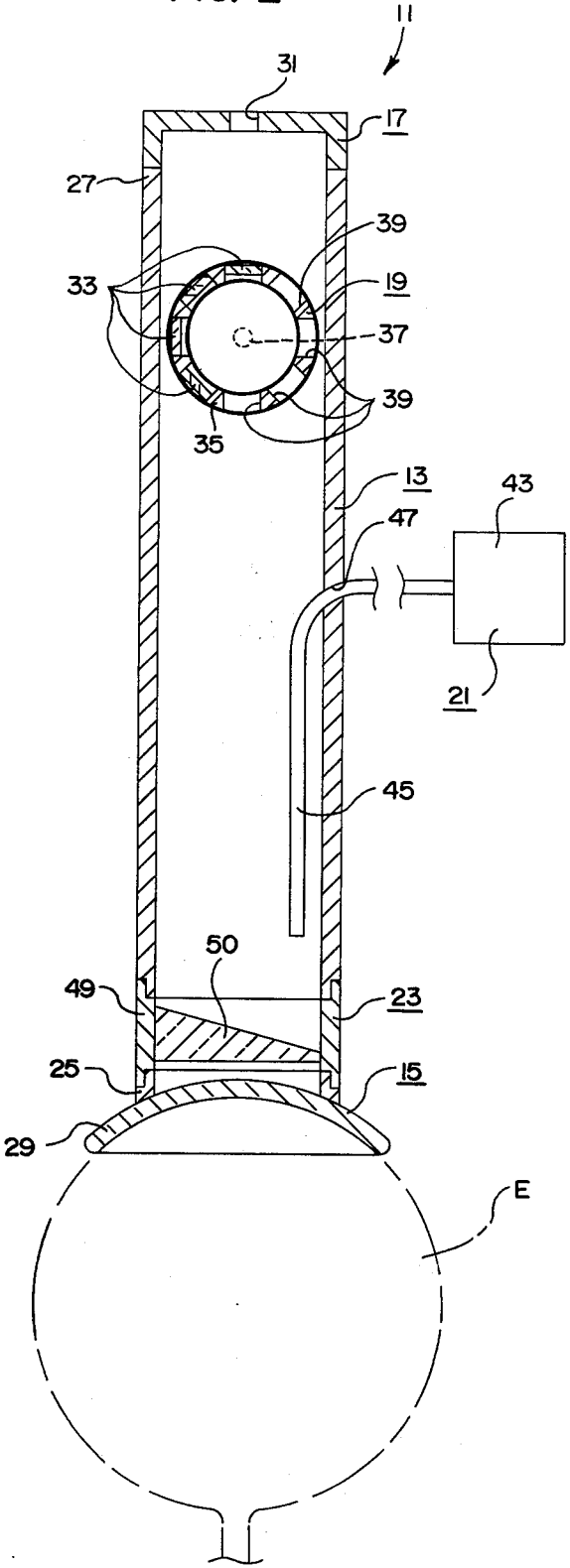

OPHTHALMOSCOPE

BACKGROUND OF THE INVENTION

1. Field of the Invention

This invention relates to ophthalmoscopes for allowing physicians to view the retina of a patient's eye.

2. Description of the Prior Art

Applicant is aware of the following U.S. patents: Allen (U.S. Pat. No. 1,116,529); Graff (U.S. Pat. No. 2,195,169); Vannas (U.S. Pat. No. 2,633,122); Kosche et al (U.S. Pat. No. 3,012,462); Keeler (U.S. Pat. No. 3,131,695); Moore et al (U.S. Pat. No. 3,439,978); Speelman (U.S. Pat. No. 3,501,228); Schenk (U.S. Pat. No. 3,586,424); and Matsura (U.S. Pat. No. 3,698,099). None of the above patents disclose or suggest the present invention.

Ophthalmoscopes can be divided into two general types according to their method of use. The first type of ophthalmoscope is illustrated by the Graff patent. In this type, the ophthalmoscope is held a substantial distance away from the patient's eye to be viewed. This spacing of the ophthalmoscope from the eye, among other disadvantages, limits the angle of view. The second type of ophthalmoscope is illustrated by the Vannas patent. In this type, the ophthalmoscope is held against or spaced only slightly from the patient's eye to be viewed. The present invention is of this second type.

One major problem with present ophthalmoscopes is that they are extremely difficult to use. In fact, special courses are typically given ophthalmologists on how to use the ophthalmoscope. Another problem with present ophthalmoscopes is that when used in retina surgery procedures, considerable clouding of the cornea occurs.

SUMMARY OF THE INVENTION

The present invention is directed towards overcoming the problems and disadvantages in prior ophthalmoscopes. The concept of the present invention is to provide an ophthalmoscope which is easily used and which substantially alleviates the problem of cloudiness of the cornea in retina surgery.

The ophthalmoscope of the present invention includes a hollow body member having an objective means for placement over the patient's eye attached to one end and having an ocular means for allowing an observer to view the patient's eye through the objective means attached to the other end. The objective means includes a contact lens member fixedly attached to the first end portion of the body member for contacting engagement with the cornea of the patient's eye. Magnification means may be positioned in the body member between the objective means and the ocular means for causing the patient's eye to be magnified as the observer view the patient's eye through the ocular means. Light means directs light into the body member and against a deflection means positioned in the body member adjacent the objective means which directs the light from the light means and the line of sight from the ocular means into the retina of the patient's eye to allow the observer to clearly view the retina of the patient's eye. The deflection means includes means for allowing the angle at which the light from the light means and the line of sight from the ocular means are being directed into the retina of the patient's eye to be changed thereby allowing the observer to view a particular area of the retina of the patient's eye.

BRIEF DESCRIPTION OF THE DRAWINGS

FIG. 1 is a front elevational view of the ophthalmoscope of the present invention.

FIG. 2 is a sectional view of the ophthalmoscope of the present invention as taken on line II—II of FIG. 1, shown in contact with a patient's eye.

FIG. 3 is a sectional view of a portion of the ophthalmoscope of the present invention showing an alternate embodiment of the deflection means.

DESCRIPTION OF THE PREFERRED EMBODIMENT

The ophthalmoscope 11 of the present invention allows an observer such as a physician to clearly and easily view the retina of a patient's eye E. The ophthalmoscope 11 includes, in general, a hollow body member 13, an objective means or member 15, an ocular means or member 17, a magnification means or member 19, a light means or member 21 and a deflection or member 23.

The hollow body member 13 is preferably straight and tubular in structure. The body member 13 includes a first end portion 25 onto which the objective member 15 is attached and includes a second end portion 27 onto which the ocular member 17 is attached.

The objective member 15 includes a contact lens member 29 of the type well known to those skilled in the art for contacting engagement with the cornea of the patient's eye E when the ophthalmoscope 11 is in use. The contact lens member 29 is fixedly attached to the first end portion 25 of the body member 13, and placed on the eye with a suitable transparent medium such as methylcellulose or the like.

The ocular member 17 includes a typical eyepiece for allowing the observer to view the patient's eye E therethrough. More specifically, the eyepiece may consist simply of an aperture 31 or any such means well known to those skilled in the art.

The magnification member 19 is positioned in the body member 13 between the objective member 15 and the ocular member 17 to cause the patient's eye E to be magnified as the observer views the patient's eye E through the ocular member 17. The magnification member 19 may be any type well known to those skilled in the art. For example, the magnification member may include a plurality of magnification lens 33, each of a different magnification power to vary the magnification of the patient's eye E. More specifically, the magnification member 19 is preferably provided with a drum 35 rotatably mounted in the body member 13 perpendicular to the axis of the body member 13 by pivots 37 which extend into the sides of the body member 13. Each of the plurality of magnification lens 33 is mounted on the drum 35 opposite an aperture 39 so that when a specific magnification lens 33 is aligned with the aperture 31 of the ocular member 17, the line of sight from the observer passes through the aperture 31 in the ocular member 17, the specific magnification lens 33, and the aperture 39 in the drum 35 which corresponds with that specific magnification lens 33. One of the pivots 37 preferably extends through the side of the body member 13 and a handle 41 is fixedly mounted thereto to allow the drum 35 to be manually turned to allow the observer to align any specific magnification lens 33 with the aperture 31 of the ocular member 17. Appropriate markings (not shown) are preferably provided on the handle 41 and body member 13 to allow the observer to readily select any specific magnification lens 33.

The light member 21 preferably includes a light source 43 and a flexible fiber optic light-conducting member for guiding the light from the light source 43 to the deflection member 23. The light source 43 is preferably located outside the body member 13 and is joined thereto by the fiber optic light-conducting member 45. The fiber optic light-conducting member 45 enters the hollow body member 13 through an aperture 47 or the like and extends to just above the deflection member 23.

The deflection member 23 may include prism means 49 for directing the light from the light source 43 and the line of sight from the ocular member 17 into the retina of the patient's eye E. The prism means 49 includes a prism 50 of a specific power for directing the light from the fiber optic light-conducting member 45 and the line of sight from the ocular member 17 into the retina of the patient's eye E at a specific angle. The prism means 49 is adapted to allow the prism 50 to be easily replaced by another prism having a different power for directing the light from the fiber optic light-conducting member 45 and the line of sight from the ocular member 17 into the retina of the patient's eye E at a different angle than the prism 50 thereby allowing an observer to view a particular area of the retina of the patient's eye E. For example, the prism means 49 may simply plug into the body member 13 in any manner well known to those skilled in the art and the prism 50 may be fixedly attached to the prism means 49. Thus, when it is desired to replace the prism 50 with a prism of a different power, the prism means 49 is simply unplugged from the body member 13 and another prism means having a prism of a different power than prism 50 fixedly attached thereto is plugged into the body member 13 in place of the prism means 49. Conversely, the deflection means 23 may include mirror means 51 for directing the light from the fiber optic light-conducting member 45 and the line of sight from the ocular member 17 into the retina of the patient's eye E. The mirror means 51 includes a mirror 52 located at a definite angle relative to the light from the fiber optic light-conducting member 45 and the line of sight from the ocular member 17 for directing the light from the fiber optic light-conducting member 45 and the line of sight from the ocular member 17 into the retina of the patient's eye E at a specific angle. The mirror 52 of the mirror means 51 may be movably mounted in the mirror means 51 to allow the light from the fiber optic light-conducting member 45 and the line of sight from the ocular member 17 to be directed into the retina of the patient's eye E at various angles thereby allowing an observer to view a particular area of the retina of the patient's eye E. On the other hand, the mirror 52 may be fixedly attached to the mirror means 51 and the entire mirror means 51 may be removable from the body member 13 so that the mirror means 51 may easily be replaced by another mirror means having a mirror fixedly attached thereto at a different angle than the mirror 52 in a manner similar to that described above relative to the prism means 49.

The ophthalmoscope 11 of the present invention is quite simple to use. After having selected the proper prism means 49 or mirror means 51 to direct the light from the fiber optic light-conducting member 45 and the line of sight from the ocular member 17 into the retina of the patient's eye E, the observer simply places the contact lens member 29 of the ophthalmoscope 11 onto the cornea of the patient's eye E and selects the proper magnification lens 33 by turning the handle 41.

As thus constructed and used, the present invention provides an ophthalmoscope 11 which is extremely simple to use, requiring only one hand to properly position and hold. In addition, the ophthalmoscope 11 decreases the likelihood of the cornea of the patient's eye E becoming cloudy during retinal surgery since it is held at all times in contacting engagement with the cornea. Also, the ophthalmoscope 11 provides a better view of the retina of the patient's eye E than any prior ophthalmoscope. Also, it should be understood that the present invention may be easily adapted to be used for laser and Xenon photocoagulation.

Although the present invention has been described and illustrated with respect to a preferred embodiment thereof, it is not to be so limited since changes and modifications may be made therein which are within the full intended scope of the invention.

I claim:

1. An ophthalmoscope for allowing an observer to view the retina of a patient's eye during retina surgery, said opthalmoscope comprising:
   a. a straight, tubular body member having a first end portion and a second end portion;
   b. objective means attached to said first end portion of said body member for placement over the patient's eye, said objective means including a contact lens member fixedly attached to said first end portion of said body member for contacting engagement with the cornea of the patient's eye;
   c. ocular means attached to said second end portion of said body member for allowing the observer to view the patient's eye through said objective means;
   d. magnification means positioned in said body member between said objective means and said ocular means for causing the patient's eye to be magnified as the observer views the patient's eye through said ocular means, said magnification means including a plurality of magnification lens for varying the magnification of the patient's eye;
   e. light means for directing light through said objective means and against the patient's eye to allow the patient's eye to be illuminated, said light means including a light source and a fiber optic light-conducting member for guiding the light from said light source to the patient's eye; and;
   f. deflection means positioned in said body member adjacent said objective means for directing the light from said fiber optic light-conducting member and the line of sight from said ocular means into the retina of the patient's eye to allow the observer to clearly view the retina of the patient's eye, said deflection means including means for allowing the angle the light from said fiber optic light-conducting member and the line of sight from said ocular means are being directed into the retina of the patient's eye to be changed thereby allowing the observer to view a particular area of the retina of the patient's eye.

2. The ophthalmoscope of claim 1 in which said deflection means includes prism means for directing the light from said fiber optic light-conducting member and the line of sight from said ocular means into the retina of the patient's eye.

3. The ophthalmoscope of claim 1 in which said deflection means includes mirror means for directing the light from said fiber optic light-conducting member and the line of sight from said ocular means into the retina of the patient's eye.

* * * * *